United States Patent
Fini et al.

(10) Patent No.: US 9,744,296 B2
(45) Date of Patent: Aug. 29, 2017

(54) MEDICAMENT APPLICATION ADAPTER COMPRISING A GAS BLOCKING ELEMENT FOR A HEMODIALYSIS TUBE SET

(75) Inventors: Massimo Fini, Mirandola (IT); Stefan Weiss, Bad Homburg (DE); Andreas Terpin, Frankfurt am Main (DE); Alain Veneroni, Spino d'Adda (IT)

(73) Assignee: FRESENIUS MEDICAL CARE DEUTSCHLAND GMBH, Bad Homberg (DE)

( * ) Notice: Subject to any disclaimer, the term of this patent is extended or adjusted under 35 U.S.C. 154(b) by 24 days.

(21) Appl. No.: 13/508,164

(22) PCT Filed: Nov. 3, 2010

(86) PCT No.: PCT/EP2010/006691
§ 371 (c)(1),
(2), (4) Date: May 4, 2012

(87) PCT Pub. No.: WO2011/054497
PCT Pub. Date: May 12, 2011

(65) Prior Publication Data
US 2012/0226236 A1    Sep. 6, 2012

(30) Foreign Application Priority Data
Nov. 4, 2009    (DE) .................. 10 2009 051 945

(51) Int. Cl.
*A61M 5/162*    (2006.01)
*A61M 5/155*    (2006.01)
(Continued)

(52) U.S. Cl.
CPC .............. *A61M 5/162* (2013.01); *A61M 1/14* (2013.01); *A61M 1/3621* (2013.01);
(Continued)

(58) Field of Classification Search
CPC .................. A61M 5/162; A61M 5/155; A61M 2005/1623; A61M 1/14; A61M 1/3627;
(Continued)

(56) References Cited

U.S. PATENT DOCUMENTS 4,175,558 A    11/1979   Hess, III et al.
4,381,776 A *  5/1983    Latham, Jr. ............... A61J 1/05
                                                    128/DIG. 24
(Continued)

FOREIGN PATENT DOCUMENTS

DE    28 30 845    1/1979
DE    38 37 298    3/1990
(Continued)

*Primary Examiner* — Bhisma Mehta
*Assistant Examiner* — Jenna Zhang
(74) *Attorney, Agent, or Firm* — Jacobson Holman, PLLC.

(57) ABSTRACT

For the administering of medicaments, an adapter is provided for connection to a haemodialysis tube set, which makes possible the direct connection of a standard injection vial to the extracorporeal circuit, avoiding the introduction of air into the circuit. The adapter has two conduit pathways. The conduit pathway for the application of medicament contains a gas-blocking element. The second conduit pathway serves for the aeration of the injection vial.

22 Claims, 3 Drawing Sheets

(51) Int. Cl.
*A61M 5/38* (2006.01)
*A61M 5/14* (2006.01)
*A61M 1/36* (2006.01)
*A61M 1/14* (2006.01)
*A61M 5/40* (2006.01)

(52) U.S. Cl.
CPC ........ *A61M 1/3627* (2013.01); *A61M 5/1411* (2013.01); *A61M 5/155* (2013.01); *A61M 5/385* (2013.01); *A61M 5/38* (2013.01); *A61M 5/40* (2013.01); *A61M 2005/1623* (2013.01); *A61M 2205/7509* (2013.01); *A61M 2205/7518* (2013.01); *A61M 2205/7527* (2013.01); *A61M 2205/7536* (2013.01)

(58) Field of Classification Search
CPC .............. A61M 1/3621; A61M 1/3659; A61M 1/3661; A61M 5/40; A61M 2205/7536; A61M 2205/7527; A61M 5/1411; A61M 5/385; A61M 1/30; A61M 2205/7509; A61M 2205/7518
USPC ................................................. 604/122–126
See application file for complete search history.

(56) References Cited

U.S. PATENT DOCUMENTS

| | | | |
|---|---|---|---|
| 4,500,309 A | 2/1985 | Diederich et al. | |
| 4,684,365 A * | 8/1987 | Reinicke | A61M 5/14276 604/126 |
| 5,015,226 A * | 5/1991 | Polaschegg | A61M 1/302 604/505 |
| 5,330,425 A | 7/1994 | Utterberg | |
| 6,261,267 B1 * | 7/2001 | Chen | A61M 5/40 604/247 |
| 7,086,431 B2 * | 8/2006 | D'Antonio | B65B 3/003 141/285 |
| 2003/0040700 A1 | 2/2003 | Hickle et al. | |
| 2007/0060902 A1 | 3/2007 | Brandenburger et al. | |
| 2008/0097315 A1 * | 4/2008 | Miner | A61M 5/1411 604/122 |
| 2011/0163030 A1 * | 7/2011 | Weaver | A61M 1/1601 210/637 |
| 2011/0275988 A1 * | 11/2011 | Davis | A61M 5/1411 604/82 |
| 2013/0218123 A1 * | 8/2013 | Beiriger | A61M 1/342 604/414 |

FOREIGN PATENT DOCUMENTS

| | | |
|---|---|---|
| EP | 0 313 348 | 4/1989 |
| EP | 0 532 432 | 3/1993 |
| EP | 0 966 631 | 9/1998 |
| EP | 1 673 135 | 4/2005 |
| IT | TO20090455 | 12/2010 |
| JP | 2002-248166 | 9/2002 |
| JP | 2005-218863 | 8/2005 |
| WO | WO 87/07159 | 12/1987 |
| WO | WO 96/29113 | 9/1996 |
| WO | WO 2010/146506 | 12/2010 |

* cited by examiner

MEDICAMENT APPLICATION ADAPTER COMPRISING A GAS BLOCKING ELEMENT FOR A HEMODIALYSIS TUBE SET

This is a national stage of PCT/EP10/006691 filed Nov. 3, 2010 and published in German, which claims the priority of German number 10 2009 051 945.9 filed Nov. 4, 2009, hereby incorporated by reference.

BACKGROUND OF THE INVENTION

1. Field of the Invention

The invention relates to a system for the administration of medicaments into extracorporeal circuits. In particular, the invention relates to an adapter which makes possible the direct connection of a standard injection vial to an extracorporeal circuit, avoiding the introduction of air into the circuit.

2. Description of the Related Art

Continuous extracorporeal circuits are used in medicine mostly for a treatment of the blood outside the patient's body. In particular in haemodialysis, blood is removed from the patient in a continuous process, the removed blood is purified by means of a dialyser and is returned immediately to the patient's blood circulation. The patient's blood is conveyed here by means of at least one pump. It usually circulates in an extracorporeal tube set which contains and connects with each other means for arterial removal, sections for conveying blood by insertion into the blood pump, connections for the dialyser, a venous drip chamber, means for the venous return of the blood to the patient and a venous drip chamber. As an alternative to such a tube set, cassette systems are also used, in which at least parts of the conduit pathways, connections and the drip chamber are integrated in an injection- or blow-moulded plastic cassette. However, the fundamental conduit pathways also remain contained in a cassette system.

The clinical picture of patients treated by means of extracorporeal circuits mostly requires the intravenous administration of medicaments. Usual medicaments for the treatment of dialysis patients comprise, for example, vitamin D and recombinant erythropoietin and iron preparations for the treatment of anaemia.

Such medicaments are usually provided in injection vials. An administration takes place by the hospital personnel, by the corresponding dose of the medicament being transferred into a disposable syringe and being administered via injection sites provided for this in the extracorporeal tube set or cassette set. In this way, the medicaments can be administered in a time-saving manner during the extracorporeal treatment and without the necessity of an additional connection of the patient for infusion.

The injection sites are mostly designed here as T-pieces which are accessible through a septum or through a Luer connector which is able to be closed off. A disadvantage of the administration through such access points is the use of an additional disposable part, the syringe, for the transfer of the medicament. Furthermore, the administration via a syringe equipped with a cannula harbours a risk of injury for the hospital personnel and a problem connected therewith in the waste management of the disposable syringes. Most medicaments are administered here as a bolus. However, there are also medicaments, such as the iron preparation Venofer for example, which are preferably administered over a longer period of time. In such a case, the manual injection is time-consuming, because the hospital personnel must be available for this task over the entire time period of the extended injection.

A similar problem to the addition of medicaments is also posed in the addition of anticoagulating agents. Outside the body, the blood tends to coagulation. Although the biocompatibility of tube- and cassette sets and of dialysers is being constantly improved, the coagulation of the blood can not be prevented without the addition of anticoagulating agents. The addition of anticoagulating agents, such as heparin or citrate, takes place in the dialysis treatment likewise via the extracorporeal circuit and preferably not as a bolus, over a certain period of time. For this purpose, most dialysis machines contain a device for the infusion of the anticoagulating agent, mostly heparin. Such heparin pumps are usually constructed as injection pumps which are automatically controlled.

DE 38 37 298 discloses the arrangement of a heparin-filled injection in the underpressure region of the extracorporeal circuit and a passive suction of the heparin into the extracorporeal circuit.

U.S. Pat. No. 5,330,425 and EP 966 631 disclose tube sets with a blow-moulded venous drip chamber with various injection sites for medicaments on the drip chamber and in the tube set behind the drip chamber.

U.S. Pat. No. 4,500,309 discloses the infusion of citrate solution into the arterial region of the extracorporeal circuit and the infusion of calcium solution into the venous region of the extracorporeal circuit.

EP 532 432 discloses the infusion of a substitute solution into the extracorporeal circuit. WO 87/07159 discloses a double-lumen transfer piece for the connection of an injection vial.

SUMMARY OF THE INVENTION

It is an object of the invention to make possible a reliable infusion into the extracorporeal circuit without the necessity of a further mechanical pump.

It is, in addition, an object of the invention to carry out the infusion directly from a standard injection vial in an automated manner, without the necessity of transfer into a syringe.

A further object is to carry out the infusion of the medicament in a small volume.

The problem is solved by a medical device, generally designated by reference numeral (40), with a piercing structure generally designated by reference numeral (42) for introduction into an injection vial (22) for the storage of medicament. The piercing structure includes a first conduit pathway (10) and a second conduit pathway (11). The first conduit pathway (10) is designed so that it opens out at one end (17) into the inner lumen of the injection vial, when the piercing structure (42) penetrates fully into the injection vial, and at the other end joins on to the conduit pathways of an extracorporeal blood circuit (19) of a haemodialysis machine. The second conduit pathway (11) is designed so that it opens out at one end (18) into the inner lumen of the injection vial, when the piercing structure (42) penetrates fully into the injection vial, and at the other end is connected with a gas reservoir (14) so that a ventilation can take place via the second conduit pathway (11). In the first conduit pathway (10) a gas-blocking element (12, 23) is arranged so that liquids can pass the gas-blocking element, but the gas-blocking element is not passable for gases.

The device can be used at various locations of the extracorporeal blood circuit, in order to introduce the content of a medicament injection vial directly into the extracorporeal blood circuit.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
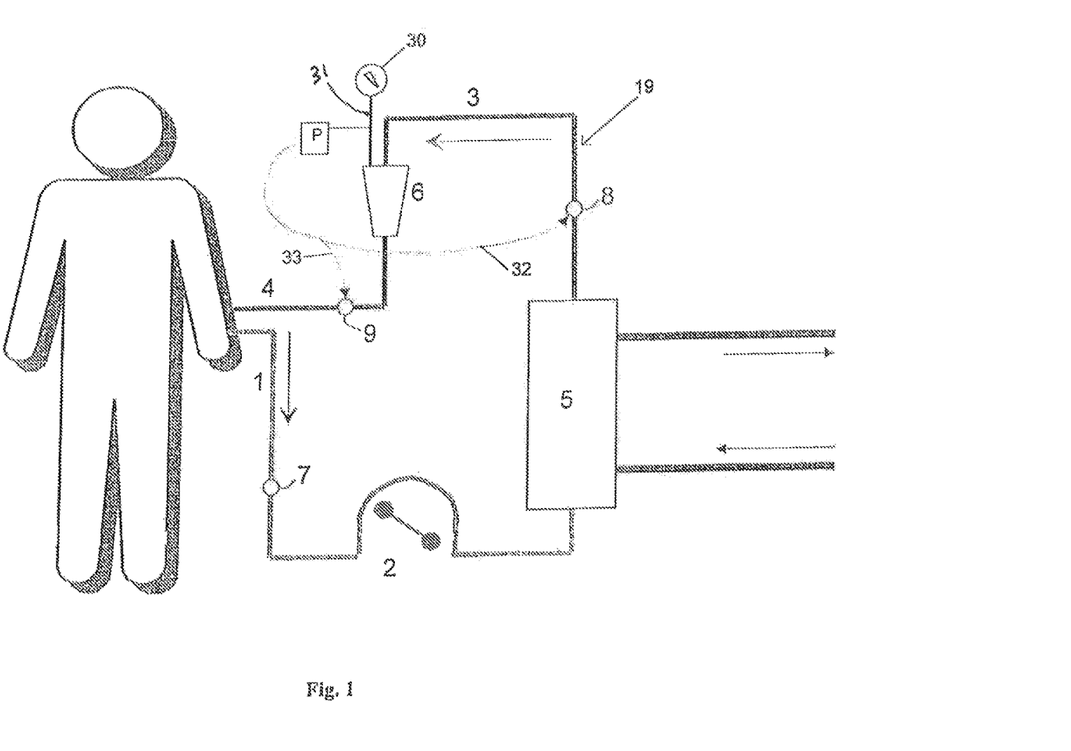
FIG. 1 shows diagrammatically an extracorporeal blood circuit of a haemodialysis.

In an extracorporeal circuit for haemodialysis, the blood is usually removed from the patient at an arterio-venous fistula. The portion of the extracorporeal circuit before the dialyser (5) is designated as arterial circuit (1), the portion of the extracorporeal circuit after the dialyser is designated as venous circuit (3, 4). A blood-conveying device (2) is normally arranged in the arterial portion of the extracorporeal circuit. The blood-conveying device is frequently embodied as a tube roll pump. In the venous portion of the extracorporeal blood circuit, mostly a venous drip chamber (6) is arranged. The venous drip chamber serves for the deaeration of the blood. In the extracorporeal circuit, but in particular on the dialyser, small quantities of air can arrive into the blood, which join each other to form small air bubbles in the blood and must not be re-infused, because the infusion of air into the natural blood circulation can cause pain and, in the worst case, can lead to embolism. In the venous drip chamber, these small air bubbles are hence eliminated.

The blood-conveying device conveys the blood through the extracorporeal circuit. It develops a suction before the portion of the circuit before the Dump, whereas the blood in the portion after the pump is moved forwards by pressure. Therefore, an underpressure prevails in the arterial circuit before the pump, whereas in the portion of the circuit after the pump an excess pressure prevails. The pressure in the venous circuit is determined by measurement at the venous drip chamber using a pressure gauge (30) or the like.

The extracorporeal blood circuit takes place in most systems entirely within a tube set or a cassette set. Such a set contains the connections for connecting the patient and for connecting to the dialyser. The drip chamber and devices for diagnostic measurements are likewise integrated in the set.

This general mode of operation also applies to haemofiltration and haemodiafiltration, which possess a higher ultrafiltration rate and replace a portion of the fluid filtered off from the blood with substitute solution. Within the framework of the present invention, haemofiltration and haemodiafiltration are therefore combined under the generic term haemodialysis.

In the tube sets there are usually also injection sites for medicaments.

The following injection sites are presented here:

An injection site (7) in the arterial blood circuit (1) before the blood-conveying device.

An injection site (8) in the venous blood circuit (3) before the venous drip chamber.

An injection site (9) in the venous blood circuit (4) after the venous drip chamber.

The injection site, mostly in the form of a T-piece with septum access, Luer access which is able to be closed off, or both types of access, in the extracorporeal blood circuit before the blood-conveying device is generally designated as arterial addition site (7). With a blood flow of zero, a slight excess pressure of approximately 100 mbar prevails at this site. With a blood flow of approximately 250 to 500 ml/min, which is usual for treatment, underpressure conditions occur at this site in the range of approximately 50 to 300 mbar. Through irregularities in the pump function of the blood conveying device, distinct fluctuations in pressure occur. The actually existing pressure is also dependent on the drop in pressure on flowing through the cannula and the tube line and also on the geodetic level difference between the patient connection and the removal site.

As a whole, this site in the extracorporeal blood circuit is suited to sucking in infusion solutions or medicament solutions via gravity infusion devices.

Figure 2:
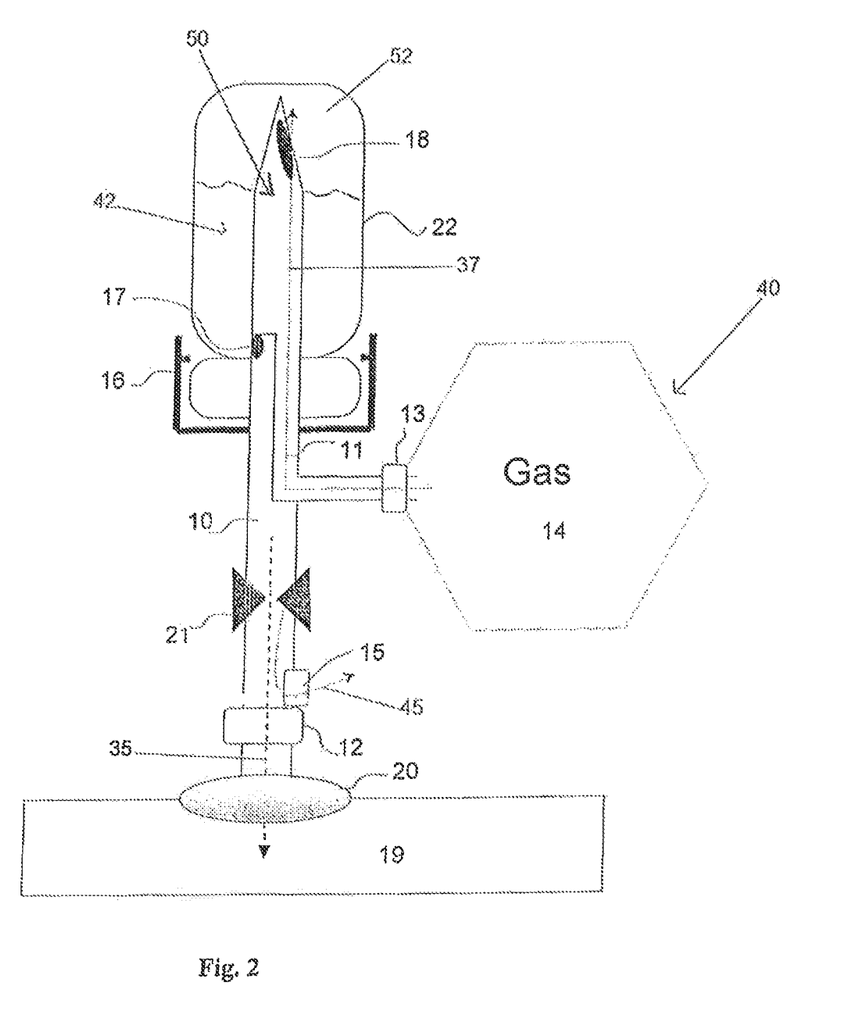
FIG. 2 shows diagrammatically a device according to the invention, a transfer piece with a double-lumen spike with an attached injection vial and the connection to the extracorporeal circuit. A hydrophilic membrane is arranged in the first conduit pathway.
Figure 3:
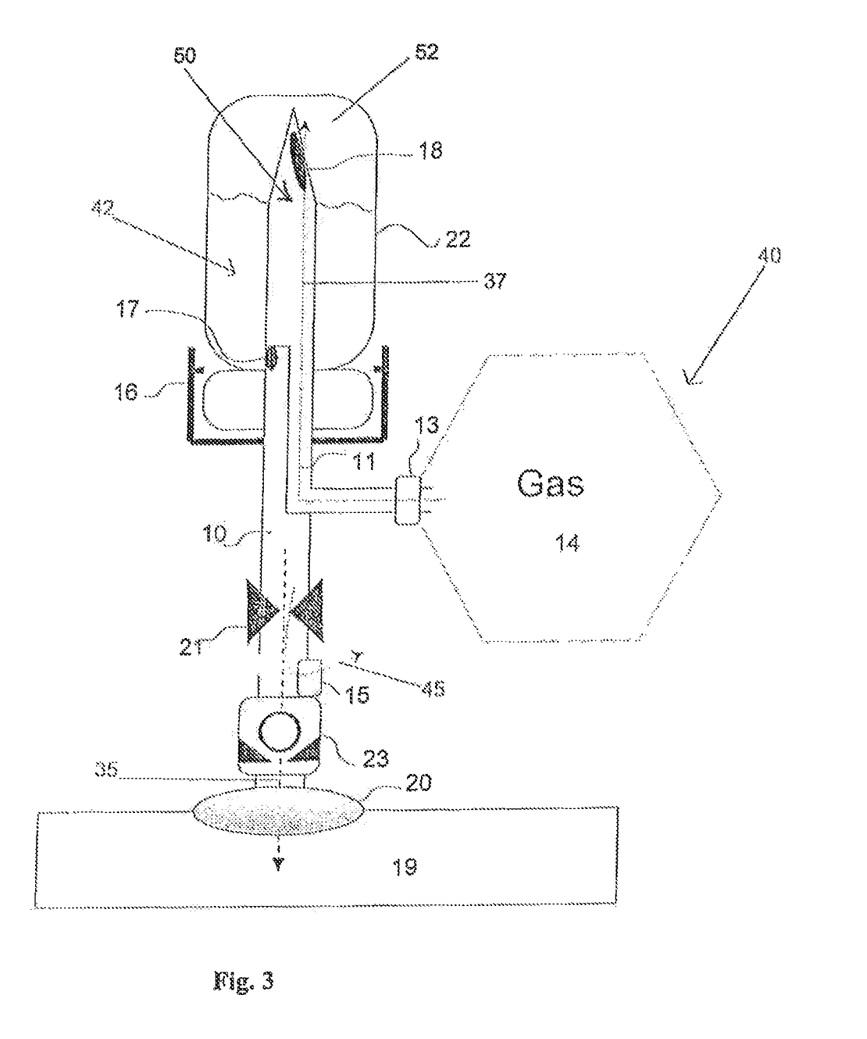
FIG. 3 shows diagrammatically an alternative device according to the invention, a transfer piece with a double-lumen spike with an attached injection vial and the connection to the extracorporeal circuit. A float valve is arranged in the first conduit pathway.

According to the invention, a medical device with a piercing structure (42) with two conduit pathways is suited for the application of a medicament which is provided in a standard injection vial (22). The piercing structure (42) with two conduit pathways can be embodied in the form of two separate hollow needles, cannulas or spikes, which are integrated into the medical device. However, the piercing structure (42) is preferably a double-lumen spike, generally designated by reference numeral (50), as shown in FIGS. 2 and 3. All the embodiments described below, in which the term spike is used, refer both to the piercing structure with two separate piercing elements and also to the preferred embodiment of the double-lumen spike (50). As illustrated in FIGS. 2 and 3, the spike, when in use according to the invention, is introduced fully into an interior (52) of the injection vial (22). Usually, the injection vial is used here with its opening downwards. The introduction of the spike is complete when both conduit pathways of the spike open out into the interior (52) of the injection vial.

In a preferred embodiment, a receiving device (16) is provided on the spike for the at least partial reception of the injection vial. The receiving device is, in addition, advantageously embodied so that it holds the injection vial in its position. For this purpose, detent noses can be provided on the receiving device, which engage behind the neck of the injection vial, in order to secure the injection vial against an unintentional uncoupling. Ideally, the receiving device is additionally embodied so that one can fit a cap in a tight manner. Such a cap is intended to close off the access in a tight manner before and after use, in order to keep contamination by the environment as low as possible. Injection sites in the extracorporeal circuit must satisfy a high standard of sterility.

When the spike penetrates fully into the injection vial (22), both conduit pathways (10, 11) must open out into the interior of the injection vial. The bearing surface of the receiving device ideally guarantees here that the spike always penetrates at an equal depth into the injection vial.

In a preferred embodiment, the medical device is embodied so that a valve only opens the fluid connection of the first conduit pathway and/or of the second conduit pathway when an injection vial is fully introduced into the medical device. Such receiving devices for the secure connection of an injection vial are known in the prior art, for example the Italian patent application TO2009A000455 discloses a suitable device.

In a particularly preferred embodiment, the medical device is adapted to the shape of the injection vial and to the thickness of the septum sealing the injection vial that the first conduit pathway (10) opens out at an end (17) into the injection vial so that the distance between the end of the conduit pathway (17) and the pierced septum is as small as possible; preferably the distance between the end of the first conduit pathway and the septum is less than 3 mm and particularly preferably less than 1 mm. The end (18) of the second conduit pathway (11) opens out in the preferred embodiment into the injection vial so that the end (18) likewise lies in the injection vial when the spike penetrates fully into the injection vial. In the preferred embodiment, the distance of the end (18) of the second conduit pathway from the septum is greater than the distance of the end (17) of the first conduit pathway; particularly preferably, the distance is greater than 3 mm and particularly preferably greater than 6 mm. In a specially preferred embodiment, the end (18) of the second conduit pathway lies above the fluid level of the fluid contained in the injection vial. In a further preferred embodiment, the diameter of the first conduit pathway is greater at every point than the diameter of the second conduit pathway.

The other end of the first conduit pathway (10) joins on to the extracorporeal blood circuit (19). In this way, a connection is created between the injection vial (22) and the extracorporeal blood circuit (19), which permits a direct application of the content of the injection vial into the extracorporeal circuit through the first conduit pathway (10) as shown by the arrowed line 35 in FIGS. 2 and 3.

When the content of the injection vial is sucked in at the arterial addition or injection site (7) into the extracorporeal circuit, the volume which is removed in this way must be replaced. Otherwise, an underpressure occurs in the interior of the rigid injection vial with respect to the pressure conditions in the extracorporeal circuit. When the pressure in the interior of the injection vial is less than that in the extracorporeal circuit, the flow of the content of the injection vial into the extracorporeal circuit terminates. In order to prevent this, the second conduit pathway (11) is connected to a gas reservoir (14), from which the volume of the content of the injection vial flowing into the extracorporeal circuit is substituted by gas, in order to thus provide for a pressure equalization. In the simplest case, the ambient air constitutes the gas reservoir. Alternatively, the gas reservoir can be constituted by a rigid or a flexible container filled with gas. In this case, the container is preferably flexible. As a further alternative, a gas-conducting line can form the gas reservoir. Whatever the form of the gas reservoir, gas flows from the reservoir into the injection vial through the second conduit pathway (11) as shown by the arrowed line 37 in FIGS. 2 and 3.

If the gas which is provided is not a sterile gas, as for instance in the case of the ambient air, ideally a gas-permeable sterile filter (13) is provided in the second conduit pathway. Such sterile filters are known to the specialist in the art and are frequently used in medical technology for the ventilation of conduit pathways whilst maintaining sterility. Sterile filters are distinguished primarily in that they have a pore size or an aperture size which does not allow microorganisms to pass this barrier. A pore size of less than 0.3 µm is preferred. In a preferred embodiment, the sterile filter is a hydrophobic filter. A hydrophobic filter with a hydrophobic filter material is not wetted or moistened by aqueous fluids and does not allow any such fluids to pass. In this way, the content of the injection vial is prevented from emerging through the second conduit pathway.

In the ideal case, the gas of the gas reservoir should not react with the content of the injection vial. Thus, for example, it can be recommended in the case of an easily oxidizable content, to provide an inert gas, such as nitrogen for example, from the reservoir, instead of air.

The gas reservoir should preferably be dimensioned so that it permits the complete emptying of the injection vial, i.e. in the case of normal pressure it should have an equally great or greater volume with respect to the injection vial.

On emptying of the injection vial, the fluid level in the injection vial falls until a level is reached which lies below the opening (17) at the end of the first conduit pathway (10). From this moment, gas enters into the first conduit pathway (10). An entry of gas into the extracorporeal circuit is to be avoided. At the addition sites (7, 8) before the venous drip chamber (6), the avoidance of the entry of gas is desirable. Although the removal of gas bubbles is indeed still possible in the venous drip chamber, gas bubbles in the extracorporeal circuit can nevertheless bring about complications and also lead, in the course of time, to an undesired drop in the fluid level in the venous drip chamber. At the addition site (9) after the venous drip chamber, the avoidance of the entry of gas is essential, because no gas bubbles are allowed to be infused into the patient. Therefore, with the use of this addition site, it is recommended to also provide a gas bubble detector after the addition site (9) in the extracorporeal circuit.

To prevent the entry of gas into the extracorporeal circuit, in the preferred embodiment the gas-blocking element is a hydrophilic membrane (12) which is integrated in a gas-tight manner into the first conduit pathway (10). In the dry state, a hydrophilic membrane is passable by fluids and also by gas. After a hydrophilic membrane was been wetted by fluids, in particular aqueous fluids, the hydrophilic membrane in the wet state is substantially impermeable to oases. Hydrophilic membranes absorb fluid quickly and are soaked thereby. The CWST forms a measure for the extent of hydrophilia of a membrane, the measurement of which is described in EP 313 348. Membranes with a CWST of greater than 72 dyn/cm are generally deemed to be hydrophilic. Corresponding membranes can be woven or non-woven porous structures. The membrane can consist of natural material, such as for example cotton, cellulose or hemp, but preferably consists of polymers of hydrophilic monomers, such as for example vinylphosphonic acid, vinylsulphonic acid, acrylic acid and methacrylic acid, vinylpyridine, 3-vinylpyridine, 2-methyl-5-vinylpyridine, 3-ethyl-4-vinylpyridine, 2,3-dimethyl-5-vinylpyridine, N-vinylpyrrolidone, 2-vinylpyrrolidone, N-vinylpyrrolidine and 3-vinylpyrrolidine, 2-methacryloxyethylphosphorylcholine, vinyl alcohol, alkylene oxides and alkylene glycols. Hydrophilic monomers preferably have at least a solubility of 50 g/l in water.

In order to be impermeable to gas in the soaked state, the pore size must be smaller than 100 µm. A pore size of less than 15 µm state is preferred, and a pore size of less than 0.3 µm is particularly preferred, because in this order of magnitude microorganisms are additionally prevented from passing the membrane. The gas impermeability of the moistened membrane is determined by the bubble pressure test (bubble point) according to the following formula:

$$\Delta p = \frac{2\sigma \cdot \cos\theta}{r}$$

Δp=pressure difference
σ=surface tension of the fluid (water=72.75 mN/m)
θ=wetting angle of the material
r=pore radius In order to guarantee a tightness with respect to gas of the moistened hydrophilic membrane, the membrane must be selected so that the actual pressure difference between the pressure in the extracorporeal circuit and the pressure in the gas reservoir is always less than Δp was calculated for the membrane according to the above formula. It is to be noted here that the pressure difference in extracorporeal circuits is not constant, but fluctuates, influenced by the pump movement.

In addition to the function as a gas barrier, the hydrophilic membrane (12) also functions as an element regulating the flow. In many cases, it is desired that the medicament is applied from the injection vial over a longer period of time. The hydrophilic membrane is a filter element and forms a flow resistance which can regulate the flow over a certain period of time. The flow is measured here as a function of the pressure difference, the filter area and the pore size of the filter element. According to the addition site, with an average pressure difference, the filter area and the pore size of the filter element can be dimensioned so that the application of the medicament is possible over a predetermined period of time.

In an alternative embodiment, the gas-blocking element is a float valve (23). Suitable float valves are known to the specialist in the art for example from DE 28 30 845. Preferably, a float valve has a cylindrical housing in which a ball is arranged floating on aqueous fluids so that it floats during the passage of fluids and in the fluid-free state rests in a gas-tight manner on a valve seat which is arranged in an annular shape in the housing.

In addition to the gas-blocking element (12, 23) optionally also further flow-regulating elements (21) can be mounted above and/or beneath the gas-blocking element. Such elements, for example in the form of valves or clamps, can also stop the flow completely. In preferred embodiments, the medical device according to the invention has at least one flow-regulating element beneath the gas-blocking element, when the device is connected with an arterial addition site (7). In another preferred embodiment, the medical device according to the invention has at least one flow-regulating element above the gas-blocking element, when the device is connected with a venous addition site (8, 9).

Advantageously, in the direct vicinity of the gas-blocking element (12, 23) a hydrophobic membrane (15) can be arranged, which is not arranged in a fluid-tight manner in the first conduit pathway (10), but rather on the side wall of the first conduit pathway forms a connection with the ambient air and is therefore suited to the de-aeration of the first conduit pathway. The presence of such a hydrophobic membrane (15) can firstly advantageously contribute to the de-aeration of the first conduit pathway of the spike directly after the connection of the injection vial. Secondly, the possibility exists that microbubbles have formed in the content of the injection vial, which cannot pass the hydrophilic membrane (12), collect there and occlude the flow through the hydrophilic membrane. The arrangement of the hydrophobic membrane (15) in the vicinity of the hydrophilic membrane (12) permits the de-aeration of the gas which has accumulated at the hydrophilic membrane (12) as indicated by the arrowed line (45). When the gas-blocking element is a float valve, the hydrophobic membrane (15) can advantageously also be arranged in the housing of the float valve.

The medical device according to the invention can be constructed as an integral component of a haemodialysis tube set. In a preferred embodiment, the medical device is, however, an adapter which is connected via a coupling site (20) to the tube set or cassette set of a haemodialysis machine. The coupling can take place via a needle or a cannula which is pierced through a septum. However, a needle-less coupling is preferred, which reduces the risk of injury to the personnel. Needle-less coupling solutions, for example via Luer connectors, are known from the prior art, such as for example from EP 1 673 135. Coupling possibilities which guarantee the sterility of the addition site are particularly preferred.

In addition to the arterial addition site (7), further addition sites are also used in dialysis technology. In particular, the arterial addition site can not be used for medicaments with a low molecular weight, because these substances are at least partially removed by the dialyser which is arranged downstream of the arterial addition site. For most low-molecular medicaments, an addition site (8) presents itself, which is arranged between the dialyser and the venous drip chamber. This arrangement offers an additional security against an infusion of gas bubbles which would be removed in the following drip chamber. For some medicaments, however, a contact with the ambient air is to be strictly avoided, whether to prevent an oxidation or owing to the toxicity of the medicament. For such medicaments, an addition site (9) presents itself, which is arranged after the venous drip chamber.

Both addition sites in the venous circuit of the tube set are arranged after the blood-conveying device (2). In the extracorporeal circuit, after the blood-conveying device, usually a peristaltic pump, different pressure conditions prevail than before the conveying device. In contrast to the arterial addition site (7), an excess pressure prevails in the extracorporeal circuit at the two venous addition sites (8, 9) with respect to the ambient atmosphere. In order to nevertheless also guarantee an introduction of the medicament into the circuit at the venous addition sites (8, 9), the injection vial must be acted upon by a pressure which permanently exceeds the pressure in the interior of the extracorporeal circuit at the addition site. For this, a gas reservoir is provided, in which a corresponding gas pressure prevails.

For the provision of a gas reservoir with a particular pressure, various preferred embodiments are taken into consideration: the connection to an external gas line with a substantially constant pneumatic pressure, the action with pressure upon a gas container by means of a mechanical pump, the compression of a deformable gas container, the production of gas in a volume-limited gas container by a chemical reaction, as known for example from EP 1 673 135.

In a preferred embodiment, the gas reservoir which is acted upon by pressure, has a pressure relief valve, in order to prevent the pressure from exceeding a critical value. In particular it must be prevented that the pressure difference to the extracorporeal circuit exceeds the value predetermined by the bubble pressure of the hydrophilic membrane.

In a further preferred embodiment, the pressure in the gas reservoir is selected so that the application of the content of the injection vial takes place over a particular period of time, wherein the increase of the pressure reduces the period of time for the application.

In several modern haemodialysis machines, a device already exists for the introduction of a pneumatic pressure into the tube system. Usually, the pressure in the venous drip chamber (6) is measured by a pressure gauge (30) which is connected via a fluid connection (31) with the air cushion in the upper region of the drip chamber (6). Frequently, a pneumatic pump (P) is also arranged at this fluid connection, by which the fluid level in the drip chamber can be regulated by the pumping in or out of air. The pneumatic pump (P) may also be connected to the venous access point (8) by line (32) or to the venous access point (9) by line (33) to apply pressure to the pressure reservoir driving the introduction of the medicament.

In a particularly preferred embodiment, a source for pneumatic pressure is used which is already present in the haemodialysis machine, in order to produce a pressure in the gas reservoir (14). The gas reservoir (14) in this case is usually simply the fluid connection to the second conduit pathway (11). The source for the pneumatic pressure is then usually the pump (P) for the introduction of air into the venous drip chamber. A control can be carried out by a valve as to whether the pump (P) is connected with the gas reservoir or with the venous drip chamber.

In a further particularly preferred embodiment, in the fluid connection between the source for the pneumatic pressure and the second conduit pathway, the pressure in the gas reservoir which is thus produced is measured by means of a further pressure measuring device. In this way, by comparison of the pressure in the gas reservoir and of the pressure in the venous drip chamber, the pressure difference can be determined. By application of the pump, the pressure in the gas reservoir can then be set so that the pressure difference, taking into consideration the flow resistance in the first conduit pathway of the medical device is precisely so great in order to administer a particular quantity of a medicament per unit of time. In this way, the administering of the medicament over a period of time is able to be regulated in an improved manner. In addition, it can thus be ensured that the pressure difference does not exceed the bubble pressure of the hydrophilic membrane.

As a further embodiment, using the pump (P), it is conceivable to place a valve which controls the connection of the pump to the gas reservoir or to the drip chamber so that a constant fluid connection exists between the pump and a pressure gauge. The one pressure gauge can then detect alternately, but not simultaneously, the pressure in the drip chamber or in the gas reservoir. An advantage in this embodiment is the saving of a pressure gauge.

In a further embodiment, the haemodialysis machine has, in addition to the pump (P) which is already present, a further additional pump, which controls the pressure in the gas reservoir. In such a case, it is preferred that the pressure in the gas reservoir is in turn measured by means of a pressure gauge, and the pressure difference from the pressure in the venous drip chamber is determined. This arrangement also makes possible the regulation of the pressure difference and hence the administering of the medicament over a particular period of time.

Examples are presented below, which are intended to contribute to the explanation of the invention, without restricting the invention in any way.

Example 1

The blood flow in the extracorporeal circuit of a haemodialysis machine is stopped by stopping the blood-conveying device (2). The cap, which seals in a sterile manner, is removed from the receiving device (16) of a medical device according to the invention which is provided with the arterial addition site (7). An injection vial containing a medicament is placed onto the medical device so that the double-lumen spike penetrates fully into the injection vial. A previously closed flow-regulating element (21) in the form of a clamp, which is mounted beneath the hydrophilic membrane, is opened. A wetting of the hydrophilic membrane (12) with blood takes place with simultaneous de-aeration of the first conduit pathway (10) through the hydrophobic membrane (15). Immediately after the wetting of the hydrophilic membrane, the blood flow is continued by placing into operation the blood-conveying device. With a connecting of the second conduit pathway (11) of the medical device to a gas reservoir (14) with atmospheric pressure, in this case ambient air, the pressure at the arterial addition site (7) falls below the atmospheric pressure. Through the pressure difference $\Delta p$, the content of the injection vial is transferred into the extracorporeal circuit and the volume in the injection vial is substituted by ambient air. After the entire content of the injection vial has been transferred into the extracorporeal circuit and also the volume in the first conduit pathway (10) has been substituted by air, the fluid flow stops through the hydrophilic membrane (12), which was not passable by gas. The flow-regulating element (21) is closed and the receiving device (16) is covered by a cap which seals in a sterile manner.

Example 2

During the continuous blood flow in the extracorporeal circuit of a haemodialysis machine, the cap, which seals in a sterile manner, is removed from the receiving device (16) of a medical device according to the invention, which is connected with a venous addition site (8, 9). An injection vial containing a medicament is placed onto the medical device so that the double-lumen spike penetrates fully into the injection vial.

The second conduit pathway (11) of the medical device is connected with a gas reservoir (14) which has a pneumatic pressure which is permanently higher than the pressure in the extracorporeal circuit at the venous addition site. A previously closed flow-regulating element (21) in the form of a clamp, which is mounted above the hydrophilic membrane, is opened. A wetting of the hydrophilic membrane (12) with blood, with simultaneous de-aeration of the first conduit pathway (10) through the hydrophobic membrane (15) has already taken place previously through the connection with the extracorporeal blood circuit, which at this point has a pressure which is greater than the atmospheric pressure. Through the pressure difference $\Delta p$ between the gas reservoir and the extracorporeal circuit at the venous addition site, the content of the injection vial is transferred into the extracorporeal circuit and the volume in the injection vial is substituted by gas from the gas reservoir. After the entire content of the injection vial has been transferred into the extracorporeal circuit and also the volume in the first conduit pathway (10) has been substituted by gas, the fluid flow stops through the hydrophilic membrane (12), which is not passable by gas. The flow-regulating element (21) is closed and the receiving device (16) is covered by a cap which seals in a sterile manner.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A medical device for introduction of a liquid medicament stored in an injection vial into an extracorporeal blood circuit of a haemodialysis machine during operation thereof, said device comprising:
   a gas reservoir for storing a gas, wherein pressure in said gas reservoir is selectable to regulate liquid medicament flow rate into the extracorporeal blood circuit and a period of time over which the liquid medicament in the injection vial is administered into the extracorporeal blood circuit, and wherein a pressure in said gas reservoir is greater than a pressure in conduit pathways of the extracorporeal blood circuit at an addition site;
   a piercing structure for opening the injection vial, said piercing structure having a first conduit pathway and a second conduit pathway,
      a first end of said first conduit pathway opening into an interior of the injection vial when said piercing structure has been inserted to penetrate fully into the interior of the injection vial,
      a second end of said first conduit pathway being joined to the conduit pathways of the extracorporeal blood circuit of the haemodialysis machine at the addition site,
      a first end of said second conduit pathway opening into the interior of the injection vial when said piercing structure has been inserted to penetrate fully into the interior of the injection vial,
      a second end of said second conduit pathway being connected with said gas reservoir so that gas held in said gas reservoir is able to flow into the interior of the injection vial via the second conduit pathway,
   a gas-blocking filter element being arranged in said first conduit pathway, said gas-blocking filter element configured to block passage of gases therethrough while allowing the liquid medicament from said injection vial to pass through the gas-blocking filter element and into the extracorporeal blood circuit of the haemodialysis machine at the addition site via said first conduit pathway, said gas-blocking filter element having a filter area and pore size dimensioned to create a desired flow resistance that, in cooperation with a selected pressure in said gas reservoir, is effective to regulate the liquid medicament flow rate from the injection vial to the extracorporeal blood circuit by increasing or decreasing the liquid medicament flow rate through said gas-blocking element so as to administer a greater or lesser quantity, respectively, of the liquid medicament to the extracorporeal blood circuit per unit of time during operation of the haemodialysis machine;
   a venous drip chamber;
   a first pressure measuring device that determines a pressure of the gas in said venous drip chamber; and
   a second pressure measuring device that determines a pressure of the gas in the said gas reservoir,
   wherein the pressure in said gas reservoir is selected based on a pressure difference determined by a comparison the pressure of the gas in said venous drip chamber with the pressure of the gas in said gas reservoir, and wherein the selected pressure is that which is required to regulate the liquid medicament flow rate into the extracorporeal blood circuit without the pressure difference exceeding a bubble pressure of said gas-blocking filter element.

2. The medical device according to claim 1, wherein the device is an integral component of a tube set or a cassette set for the construction of the extracorporeal blood circuit of a haemodialysis.

3. The medical device according to claim 1, wherein the piercing structure is an adapter for connection to a tube set or to a cassette set of the extracorporeal circuit of the haemodialysis machine.

4. The medical device according to claim 3, wherein the adapter is configured such that the connection with the extracorporeal circuit is effected in a needleless manner.

5. The medical device according to claim 1, further comprising a receiving device that is closable by a cap.

6. The medical device according to claim 1, further comprising a hydrophobic membrane which is arranged in said first conduit pathway so that said hydrophobic membrane forms a connection to ambient air such that said hydrophobic membrane does not close said first conduit pathway in a fluid-tight manner.

7. The medical device according to claim 1, further comprising a hydrophobic sterile filter arranged in said second conduit pathway.

8. The medical device according to claim 1, further comprising a flow-regulating element arranged in said first conduit pathway above and/or beneath said gas-blocking element.

9. The medical device according to claim 1, wherein said piercing device is a double-lumen spike.

10. The medical device according to claim 1, wherein said gas-blocking element is a hydrophilic membrane, wherein said hydrophilic membrane in a wet state creates said desired flow resistance to the liquid medicament and is impassable to gas.

11. The medical device according to claim 10, wherein said hydrophilic membrane has a pore size of less than 100 µm.

12. The medical device according to claim 10, wherein said hydrophilic membrane has a material construction of a hydrophilic polymer.

13. The medical device according to claim 10, wherein said hydrophilic membrane is gas-tight, with a bubble pressure which corresponds to the pressure difference between said gas reservoir and the extracorporeal circuit.

14. The medical device according to claim 1, wherein said gas-blocking element is a hydrophilic membrane, wherein said hydrophilic membrane in a wet state creates said desired flow resistance to the liquid medicament and is impassable to gas, and said hydrophilic membrane has a pore size of less than 15 µm.

15. The medical device according to claim 1, wherein said gas-blocking element is a hydrophilic membrane, wherein said hydrophilic membrane in a wet state creates said desired flow resistance to the liquid medicament and is impassable to gas, and said hydrophilic membrane has a pore size of less than 0.3 µm.

16. The medical device according to claim 1, wherein said selected pressure is applied to said gas reservoir by a pump.

17. A medical device for introducing a liquid medicament contained in an injection vial into an extracorporeal blood circuit of a haemodialysis machine during operation thereof, said device comprising
- a gas reservoir for storing a gas, wherein said gas reservoir is acted upon by pressure that enables a particular pressure in said gas reservoir to be set to control a liquid medicament flow rate from the injection vial into the extracorporeal blood circuit during operation of the haemodialysis machine, and wherein pressure in said gas reservoir is greater than a pressure in conduit pathways of the extracorporeal blood circuit at an addition site;
- a piercing structure for opening the injection vial, said piercing structure having a first conduit pathway and a second conduit pathway,
- a first end of said first conduit pathway and a first end of the second conduit pathway opening into an interior of the injection vial when said piercing structure has been inserted to penetrate fully into the interior of the injection vial,
- a second end of said first conduit pathway being joined to the conduit pathways of the extracorporeal blood circuit of the haemodialysis machine at the addition site,
- a second end of said second conduit pathway being in fluid communication with said gas reservoir so that gas held in the gas reservoir is able to flow into the interior of the injection vial via the second conduit pathway,
- a gas-blocking element configured to block passage of gases therethrough while, at the same time, allowing the liquid medicament flowing through said first conduit pathway from said injection vial to pass through said gas-blocking element and into the extracorporeal blood circuit of the haemodialysis machine under the pressure of the gas that flows from said gas reservoir into the interior of the injection vial via said second conduit pathway, wherein said gas-blocking element forms a flow resistance that, in cooperation with the particular pressure set in the gas reservoir, is effective to administer a particular quantity of the liquid medicament from the injection vial into the extracorporeal blood circuit per unit of time during operation of the haemodialysis machine;
- a venous drip chamber;
- a first pressure measuring device that determines a pressure of the gas in the venous drip chamber; and
- a second pressure measuring device that determines a pressure of the gas in the gas reservoir,
- wherein the pressure in the gas reservoir is selected based on a pressure difference determined by a comparison of the pressure of the gas in said venous drip chamber with the pressure of the gas in said gas reservoir so as to regulate the liquid medicament flow rate into the extracorporeal blood circuit without the pressure difference exceeding a bubble pressure of the gas-blocking filter element while taking into account a pore size and filter area of said gas-blocking element so as to effect different liquid medicament flow rates through said gas-blocking element and into the extracorporeal blood circuit and to regulate a corresponding period of time over which the liquid medicament in the injection vial is administered into the extracorporeal blood circuit for each of said different liquid medicament flow rates through said gas-blocking element.

18. The medical device according to claim 17, wherein said selected pressure is applied to said gas reservoir by a pump.

19. The medical device according to claim 17, wherein an increase in said gas reservoir pressure increases the liquid medicament flow rate through said gas-blocking element and reduces the corresponding period of time of liquid medicament administration.

20. The medical device according to claim 17, wherein a decrease in said gas reservoir pressure decreases the liquid medicament flow rate through said gas-blocking element and increases the corresponding period of time of liquid medicament administration.

21. A device for regulated introduction of a liquid medicament, said device comprising:
- an injection vial containing the liquid medicament;
- a venous drip chamber, the venous drip chamber having a first pressure measuring device that determines a pressure of a gas therein;
- a gas reservoir containing the gas, the gas reservoir having a second pressure measuring device that determines a pressure of the gas therein;
- a piercing structure for opening said injection vial; and
- a gas-blocking filter element;
- a pressure of the gas in the gas reservoir being selectable to regulate a liquid medicament flow rate,
- said piercing structure having a first conduit pathway and a second conduit pathway, a first end of said first conduit pathway opening into an interior of the injection vial, a second end of said first conduit pathway being joined to conduit pathways at a liquid medicament introduction site for haemodialysis, a first end of the second conduit pathway opening into said interior of said injection vial, and a second end of said second conduit pathway being connected with said gas reservoir,
- said gas-blocking filter element being arranged in said first conduit pathway and being configured to block passage of the gas therethrough while allowing passage of the liquid medicament therethrough,
- said gas-blocking filter element having a filter area and pore size dimensioned to provide a desired flow resistance that, in cooperation with said selected pressure of the gas in the gas reservoir, is effective to regulate the liquid medicament flow rate from said injection vial to the introduction site,
- wherein, the pressure of the gas reservoir is selected based on a pressure difference determined by comparison of the pressure of the gas in the venous drip chamber with the pressure of the gas in the gas reservoir so as to determine the pressure of the gas in the gas reservoir that is required to regulate the liquid medicament flow rate without the pressure difference exceeding a bubble pressure of the gas-blocking filter element.

22. The device according to claim 21 wherein an increase or a decrease in the liquid medicament flow rate through said gas-blocking element administers, respectively, a greater or a lesser quantity of the liquid medicament per unit of time.

* * * * *